United States Patent [19]
Othel-Jacobsen et al.

[11] Patent Number: 5,098,374
[45] Date of Patent: Mar. 24, 1992

[54] DEVICE FOR THE PLACING OF A PARTIAL CATHETER IN A BODY CAVITY

[75] Inventors: Erik Othel-Jacobsen, Hellebeak; Ole G. Neiben, Copenhagen; Henrik Harboe, Bronshoj, all of Denmark

[73] Assignee: Engineers & Doctors A/A, Copenhagen, Denmark

[21] Appl. No.: 460,190

[22] PCT Filed: Sep. 2, 1988

[86] PCT No.: PCT/DK88/00146
§ 371 Date: Jan. 31, 1990
§ 102(e) Date: Jan. 31, 1990

[87] PCT Pub. No.: WO89/01798
PCT Pub. Date: Mar. 9, 1989

[30] Foreign Application Priority Data
Sep. 2, 1987 [DK] Denmark .......................... 4587/87

[51] Int. Cl.[5] .............................. A61M 5/00
[52] U.S. Cl. .......................... 604/8; 623/12; 606/108
[58] Field of Search ............... 604/264–266, 604/280–283, 8; 606/108, 192, 194, 195, 198; 623/12

[56] References Cited

U.S. PATENT DOCUMENTS

| | | | |
|---|---|---|---|
| 4,512,338 | 4/1985 | Balko et al. | 606/195 |
| 4,531,933 | 7/1985 | Norton et al. | 604/8 |
| 4,713,049 | 12/1987 | Carter | 604/8 |
| 4,790,810 | 12/1988 | Pugh, Jr. et al. | 604/8 |
| 4,813,925 | 3/1989 | Anderson, Jr. et al. | 604/281 |
| 4,820,262 | 4/1989 | Finney | 604/8 |
| 4,820,298 | 4/1989 | Leveen et al. | 606/194 |
| 4,922,905 | 5/1990 | Strecker | 606/195 |
| 4,950,227 | 8/1990 | Savin et al. | 606/192 |
| 4,969,458 | 11/1990 | Wiktor | 606/108 |

Primary Examiner—Stephen C. Pellegrino
Assistant Examiner—Michael Rafa
Attorney, Agent, or Firm—Finnegan, Henderson, Farabow, Garrett & Dunner

[57] ABSTRACT

Device consisting of an auxiliary catheter (9), a fastening element (13), and a blocking device (11), designed in such a way that a partial catheter (2) can be mounted and secured at the end of the auxiliary catheter until the partial catheter has been placed in the desired position in a body cavity, especially the urethra, after which the partial catheter can be detached from the auxiliary catheter by manipulation of the blocking device and the fastening element, so that only the partial catheter is left in the desired position in the body cavity.

16 Claims, 2 Drawing Sheets

U.S. Patent    Mar. 24, 1992    Sheet 1 of 2    5,098,374
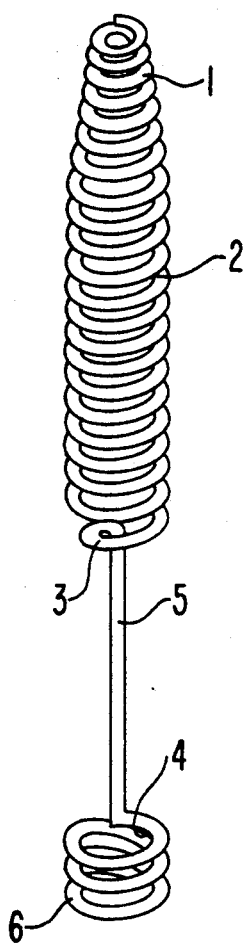
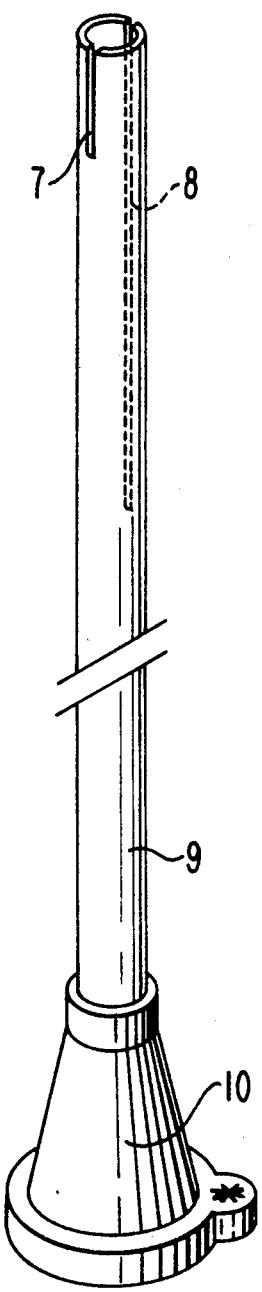
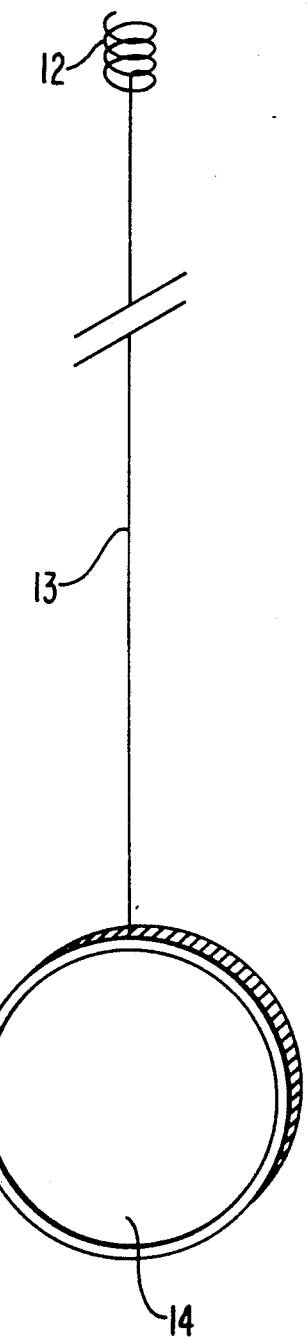
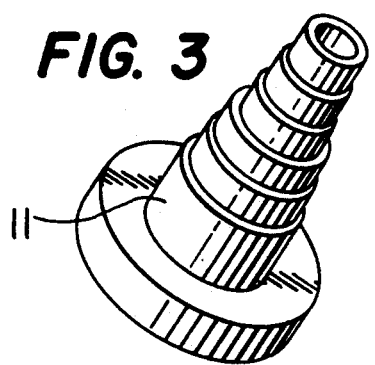

DEVICE FOR THE PLACING OF A PARTIAL CATHETER IN A BODY CAVITY

The invention concerns a device comprising an auxiliary catheter and a fastening element with a blocking device for the placing of a partial catheter in a body cavity.

The invention chiefly concerns an instrument for the placing of a partial catheter in the form of a spirally coiled metal wire in a urethra in men and especially in the part of the urethra that is located in the prostate. It will also be possible to apply the device according to the invention for the placing of partial catheters in other body cavities such as the oesphagus, the biliary passage, the intestine, or the trachea.

Equipment for the placing of partial catheters in e.g. the biliary passage is known. A considerable disadvantage in the equipment already known is that it does not comprise an independent device for securing the partial catheter during the placing procedure. A further disadvantage in the equipment already known is that the equipment ends where the partial catheter begins, so that a very flexible partial catheter and particularly a spirally coiled metal wire catheter is very unstable during the process of placing.

The purpose of the present invention is to eliminate these disadvantages.

This purpose is achieved in accordance with the invention by means of an instrument which is characteristic in that a flexible auxiliary catheter, preferably made of a plastic material, which is partly slotted at one end, is introduced into the partial catheter, and that the partial catheter is secured in its position in relation to the auxiliary catheter by means of a fastening element, preferably made of stainless steel, which is led through the auxiliary catheter up to the slotted part, where a spirally coiled part of the fastening element clutches in the auxiliary catheter as a consequence of the slotting of the auxiliary catheter.

The auxiliary catheter and the fastening element are adjusted to each other in such a way that the fastening element sticks out of the catheter at the opposite end from the slotting, whereby the auxiliary catheter and the fastening element can be manipulated in relation to each other by rotary movements or pulling/pushing movements.

If the interior of the fastening element is suitably shaped, a movement of the fastening element will imply that it is detached from the partial catheter, after which the auxiliary catheter together with the fastening element can be pulled out of the partial catheter and after that out of the urethra.

When the equipment is used in accordance with the invention for the placing of a spirally coiled metal wire catheter in the urethra in a man, the placing procedure is carried out mainly under local anesthesia of the urethra and under indirect visualization of the position of the partial catheter by means of ultra-sound or radioscopy. In the last-mentioned case the auxiliary catheter and the fastening element can be provided with one or more radiopaque markers.

In the following the invention will be described in greater detail with reference to the drawing, where FIG. 1 shows a perspective picture of a preferred embodiment of a partial catheter.

FIG. 2 shows a perspective picture of a preferred embodiment of the auxiliary catheter.

FIG. 3 shows a perspective picture of a preferred embodiment of a blocking device for the fastening element in relation to the auxiliary catheter in the partial catheter.

FIG. 4 shows a perspective picture of a preferred embodiment of the fastening element.

Figure 5:
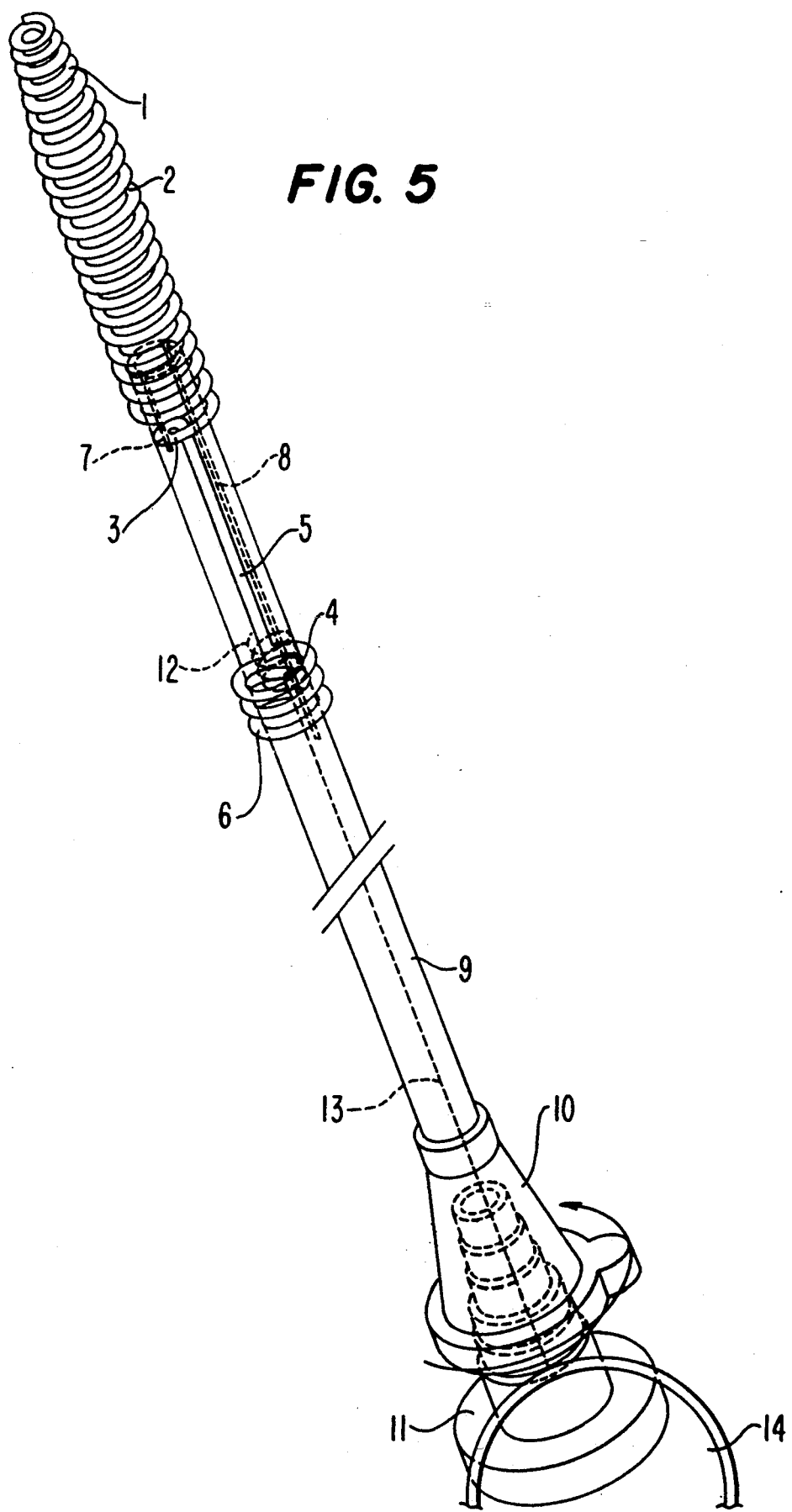
FIG. 5 shows a perspective picture of all the assembled parts of a preferred embodiment of the device in accordance with the invention.

In the drawing 1 indicates a tapered end coil of a spirally coiled metal wire catheter 2, preferably made of stainless, acid-resisting steel with a coating of gold. 3 and 4 indicate rods bent radially to the centre of the catheter and connected by a longitudinal, preferably 20 mm long rod 5. The rods 3 and 4 are preferably shifted 180 degrees in relation to each other. 6 indicated final turns in the lower end of the spiral which forms an attachment number on the catheters 2. 7 and 8 indicate partial, longitudinal slots in the upper end of the auxiliary catheter, preferably made in such a way that the one slot 7 is seven mm long and more than 20 mm shorter than the other slot 8, and that the two slots 7 and 8 are shifted 180 degrees in relation to each other, whereby it becomes possible for the two rods 3 and 4 to slide down into the slots. When the upper rod 3 slides down to the bottom of a preferred embodiment of the slot 7, further introduction of the auxiliary catheter 9 into the partial catheter 2 is stopped. 10 indicates a conical form of the lower end of the auxiliary catheter 9. 11 shows a funnel in the form of a stepped truncated cone, where the external taper of the cone is the same as the taper of the internal wall of the conical form 10 of the lower end of the catheter 9. 12 shows a spirally coiled form of the upper end of the fastening element, preferably made of one continuous piece of stainless steel wire. The spirally coiled part 12 is preferably made as five counter-clockwise turns with an outer diameter allowing the spirally coiled part 12 to be moved freely backwards and forwards in the lumen of the auxiliary catheter. The turns of the spirally coiled part 12 have a pitch and a internal diameter enabling the spiral to be screwed up around the lower part of the longitudinal rod 5 of the partial catheter 2 by axial rotation of the fastening element 13. If the length of the auxiliary catheter 9 is adjusted to the length of the fastening element 13, a 900 degrees screwing movement in order to connect the spiral 12 and the rod 5 will imply that the rod 3 is drawn tightly to the bottom of the slot 7, where it is stopped, while at the same time the fastening element 13 sticks five mm out of the conical opening 10 of the auxiliary catheter 9. 14 indicates a disc-shaped handle preferably made of a plastic material cast around the lower end of the fastening element 13. After the mounting further rotation of the fastening element 13 is prevented by the funnel 11 being pressed partly into the interior of the conical part 10 of the auxiliary catheter 9, so that the disc-shaped handle 14 is blocked. The blocking is further secured by the fact that after the mounting much more than five mm of the funnel 11 protrudes from the conical part 10 of the auxiliary catheter 9, so that rotation of the handle is blocked.

We claim:

1. A device for placing a partial catheter in a body cavity comprising:
a partial catheter having an open end and an attachment member spaced from said open end;
an auxiliary catheter onto which a portion of said partial catheter removable extends;

a fastening element extending through said auxiliary catheter, said fastening element having at one end a means for releasably connecting to said attachment member of said partial catheter;

means for selectively holding said partial catheter in place on said auxiliary catheter; and means for selectively releasing said partial catheter from said fastening member;

whereby said partial catheter, auxiliary catheter and fastening element can be inserted into the body cavity to position the partial catheter in place and the partial catheter can then be selectively released from said auxiliary catheter and said fastener element and left in said body cavity after the auxiliary catheter and fastening element are removed.

2. A device for placing a partial catheter in a body cavity comprising:

a partial catheter having an open end and an attachment member spaced from said open end;

an auxiliary catheter onto which a portion of said partial catheter removable extends, said auxiliary catheter including at least one elongated slot into which a portion of said partial catheter fits, thereby preventing relative rotation between said partial catheter and said auxiliary catheter; and a fastening element associated with said auxiliary catheter, said fastening element having at one end a means for releasably connecting to said attachment member of said partial catheter and holding said partial catheter in place on said auxiliary catheter;

means for selectively releasing said partial catheter from said fastening member;

whereby said partial catheter, auxiliary catheter and fastening element can be inserted into the body cavity to position the partial catheter into place and the partial catheter can then be selectively released from said auxiliary catheter and said fastening element and left in said body cavity after the auxiliary catheter and fastening element are removed.

3. The device of claim 2 wherein said auxiliary catheter is made of a plastic material.

4. A device for placing a partial catheter in a body cavity comprising:

a partial catheter having an open end and an attachment member spaced from said open end, said partial catheter including an elongated rod formed between said open end of said partial catheter and said attachment member of said partial catheter;

an auxiliary catheter onto which a portion of said partial catheter removable extends;

a fastening element associated with said auxiliary catheter, said fastening element having at one end a means for releasably connecting to said attachment member of said partial catheter and holding said partial catheter in place on said auxiliary catheter; and means for selectively releasing said partial catheter from said fastening member;

whereby said partial catheter, auxiliary catheter and fastening element can be inserted into the body cavity to position the partial catheter in place and the partial catheter can then be selectively released from said auxiliary catheter and said fastener element and left in said body cavity after the auxiliary catheter and the fastening element are removed.

5. The device of claim 4 wherein said partial catheter includes a first elongated spiral coil; said elongated rod being connected at one end to said first spiral coil, and a second spiral coil forming said attachment member, connected to the other end of said elongated rod opposite said first elongated spiral coil.

6. The device of claim 5 wherein said fastening element includes a third spiral coil sized to rotatably interconnect with said second spiral coil of said partial catheter, an elongated middle portion, and a handle portion spaced from said third spiral coil.

7. A device for placing a partial catheter in the urethra of a male comprising:

a partial catheter including a first elongated spiral coil having an open end, an intermediate rod being connected at one end too said first elongated spiral coil, and an attachment member connected to said intermediate rod opposite said first spiral coil;

an auxiliary catheter onto which a portion of said partial catheter removably extends;

a fastening element extending through said auxiliary catheter, said fastening element having at one end means for releasably connecting to said attachment member of said partial catheter;

a plug sized to snugly fit within a portion of said auxiliary catheter and against said fastening element to selectively hold said partial catheter in place on said auxiliary catheter; and means for selectively releasing said partial catheter from said fastening element;

whereby said partial catheter, auxiliary catheter and fastening element can be inserted into the urethra to position the partial catheter in place and the partial catheter can then be selectively released from said auxiliary catheter and said fastening element and left in said urethra after the auxiliary catheter and fastening element are removed.

8. The device of claim 7 wherein said partial catheter is made of stainless steel with a coating of a bio-compatible material to prevent crystalline growth.

9. The device of claim 8 wherein said bio-compatible material is gold.

10. A device for placing a partial catheter in a body cavity comprising:

a partial catheter having an open end and an attachment member spaced from said open end;

an auxiliary catheter onto which a portion of said partial catheter removable extends;

a fastening element extending through said auxiliary catheter, said fastening element having at one end a means for releasably connecting to said attachment member of said partial catheter;

means for selectively holding said partial catheter in place on said auxiliary catheter, said means including a plug sized to snugly fit within a portion of said auxiliary catheter and against said fastening element to hold said fastening element relative to said auxiliary catheter; and means for selectively releasing said partial catheter from said fastening member;

whereby said partial catheter, auxiliary catheter and fastening element can be inserted into the body cavity to position the partial catheter in place and the partial catheter can then be selectively released from said auxiliary catheter and said fastening element and left in said body cavity after the auxiliary catheter and fastening element are removed.

11. The device in claim 10 wherein said means for selectively releasing said partial catheter from said fastening member includes a handle secured to an end of said fastening member and extending beyond the end of said auxiliary catheter opposite said partial catheter.

12. The device in claim 11 wherein said auxiliary catheter has a first elongated portion which is cylindrical in shape and a second portion at its end opposite said partial catheter which is conical in shape.

13. The device in claim 12 wherein said plug is sized to snugly fit within the conical end of said auxiliary catheter.

14. The device of claim 13 wherein said partial catheter includes an first elongated spiral coil; an elongated rod being connected at one end too said first spiral coil, and a second spiral coil forming said attachment member and connected to the other end of said elongated rod opposite said first elongated spiral coil.

15. The device of claim 14 wherein said partial catheter has a first radially extending rod proximate said first elongated spiral coil and a second radially extending rod proximate said second spiral coil and wherein said auxiliary catheter includes a slot into which at least one of said first and second radially extending rods project, thereby preventing the relative rotation of said partial catheter and said auxiliary catheter.

16. The device of claim 15 wherein said auxiliary catheter includes a pair of slots; each slot having a different length; said first and second radially extending rods each respectively fitting into one of said slots.

* * * * *

UNITED STATES PATENT AND TRADEMARK OFFICE
CERTIFICATE OF CORRECTION

PATENT NO. : 5,098,374

DATED : March 24, 1992

INVENTOR(S) : Othel-Jacobsen et al.

It is certified that error appears in the above-identified patent and that said Letters Patent is hereby corrected as shown below:

```
Claim 1, Column 2, line 68, change "removable" to
    --removably--.

Claim 2, Column 3, line 21, change "removable" to
    --removably".

Claim 4, Column 3, line 50, change "removable" to
    --removably".

Claim 7, Column 4, line 13, change "too" to --to--.

Claim 10, Column 4, line 46, change "removable" to
    --removably--.

Claim 14, Column 5, line 14, change "too" to --to--.
```

Signed and Sealed this

Twenty-eighth Day of September, 1993

*Attest:*

BRUCE LEHMAN

*Attesting Officer*     *Commissioner of Patents and Trademarks*